United States Patent
Findlay et al.

(10) Patent No.: US 11,382,606 B2
(45) Date of Patent: Jul. 12, 2022

(54) SKIN PATCH

(71) Applicant: TFM INVENTIONS LIMITED, London (GB)

(72) Inventors: Ewan Findlay, Milnathort (GB); Sara Murray, London (GB)

(73) Assignee: TFM Inventions Limited, London (GB)

( * ) Notice: Subject to any disclaimer, the term of this patent is extended or adjusted under 35 U.S.C. 154(b) by 518 days.

(21) Appl. No.: 16/062,071

(22) PCT Filed: Dec. 16, 2016

(86) PCT No.: PCT/GB2016/053977
§ 371 (c)(1),
(2) Date: Jun. 13, 2018

(87) PCT Pub. No.: WO2017/109464
PCT Pub. Date: Jun. 29, 2017

(65) Prior Publication Data
US 2019/0000427 A1 Jan. 3, 2019

(30) Foreign Application Priority Data

Dec. 22, 2015 (GB) .................................. 1522662

(51) Int. Cl.
*A61B 10/00* (2006.01)
*G01N 33/487* (2006.01)
(Continued)

(52) U.S. Cl.
CPC ........ *A61B 10/0064* (2013.01); *A61B 5/1477* (2013.01); *A61B 5/14517* (2013.01);
(Continued)

(58) Field of Classification Search
CPC . A61B 10/0064; A61B 5/6833; A61B 5/1477; A61B 5/4266; A61B 5/4833;
(Continued)

(56) References Cited

U.S. PATENT DOCUMENTS 4,960,467 A * 10/1990 Peck .................. A61B 10/0064
600/362
5,899,856 A * 5/1999 Schoendorfer ...... A61B 5/4266
600/362
(Continued)

FOREIGN PATENT DOCUMENTS

EP 2 682 745 A1 1/2014
WO WO 92/03731 A1 3/1992
(Continued)

OTHER PUBLICATIONS

Morris et al., "Bio-sensing textile based patch with integrated optical detection system for sweat monitoring." Sensors and Actuators B: Chemical 139.1 (2009): 231-236 (Year: 2009).*

(Continued)

*Primary Examiner* — Jacqueline Cheng
*Assistant Examiner* — Tho Q Tran
(74) *Attorney, Agent, or Firm* — Haynes and Boone, LLP (57) ABSTRACT

The application relates to a chemical monitoring system comprising a skin patch for detecting an analyte in perspiration and a processor adapted to receive parameter data and to return an output indicative of a presence of an analyte in a subject's body based on the parameter data. The skin patch (100) includes a first layer (105) permeable to perspiration; a second layer (110) coupled to the first layer, the second layer being adapted to receive the perspiration; wherein a property of the second layer changes upon receiving the analyte; an electrical detector coupled to the second layer, adapted to detect parameter data indicative of the property of (Continued)

the second layer; and a flexible electronic circuit (140) coupled to the second layer, comprising a readout circuit for reading parameter data from the electronic detector and a transmitter adapted to transmit the parameter data to a processor.

19 Claims, 6 Drawing Sheets

(51) Int. Cl.
 *A61B 5/1477* (2006.01)
 *A61B 5/00* (2006.01)
 *A61B 5/145* (2006.01)

(52) U.S. Cl.
 CPC .......... *A61B 5/4266* (2013.01); *A61B 5/4833* (2013.01); *A61B 5/6833* (2013.01); *G01N 33/48714* (2013.01); *A61B 5/6829* (2013.01); *A61B 5/6831* (2013.01); *A61B 5/6898* (2013.01); *A61B 2010/0009* (2013.01); *A61B 2560/0412* (2013.01); *A61B 2562/166* (2013.01); *A61B 2562/185* (2013.01)

(58) Field of Classification Search
 CPC ........ A61B 5/14517; A61B 2010/0009; A61B 5/6829; A61B 5/6831; A61B 5/6898; A61B 2560/0412; A61B 2562/166; A61B 2562/185; G01N 33/48714; G01N 33/00
 USPC ......................................................... 600/346
 See application file for complete search history.

(56) References Cited

U.S. PATENT DOCUMENTS

| | | | | |
|---|---|---|---|---|
| 9,011,779 | B1* | 4/2015 | Anglin, Jr | G01N 33/54373 422/98 |
| 2002/0115921 | A1 | 8/2002 | Berlin | |
| 2004/0096410 | A1* | 5/2004 | Maley | A61K 31/00 424/70.1 |
| 2007/0027383 | A1* | 2/2007 | Peyser | A61B 5/1486 600/347 |
| 2013/0053668 | A1 | 2/2013 | Lin | |
| 2015/0011852 | A1 | 1/2015 | Van Kesteren et al. | |
| 2015/0056099 | A1 | 2/2015 | Peeters | |
| 2015/0057515 | A1 | 2/2015 | Hagen et al. | |
| 2015/0112165 | A1 | 4/2015 | Heikenfeld | |
| 2016/0081587 | A1* | 3/2016 | Ghazarian | A61B 5/11 600/301 |
| 2017/0325724 | A1* | 11/2017 | Wang | A61B 5/1486 |

FOREIGN PATENT DOCUMENTS

| | | |
|---|---|---|
| WO | WO 2006/007472 A2 | 1/2006 |
| WO | WO 2011/008581 A2 | 1/2011 |
| WO | WO 2013/152087 A2 | 10/2013 |
| WO | WO 2015/011852 | 1/2015 |
| WO | WO 2015/058055 A1 | 4/2015 |
| WO | WO 2015/058064 A1 | 4/2015 |
| WO | WO 2015/184065 A1 | 12/2015 |
| WO | WO 2015/184084 A2 | 12/2015 |
| WO | WO 2015/184097 A2 | 12/2015 |
| WO | WO 2016/007944 A2 | 1/2016 |
| WO | WO 2016/049019 A1 | 3/2016 |

OTHER PUBLICATIONS

PCT Search Report and Written Opinion dated Mar. 17, 2018 in corresponding International Application No. PCT/GB2016/053977.
Search Report dated Apr. 21, 2016 from corresponding Great Britain Application No. GB1522662.4.
Notice of acceptance for patent application, Australia Application No. 2016378935, dated Nov. 12, 2020, 4 pages.
Examination Report No. 1 for standard patent application, Australia Application No. 2016378935, dated Sep. 3, 2020, 6 pages.
Swift, R. M., et al., "Studies on a wearable, electronic, transdermal alcohol sensor." Alcoholism: Clinical and Experimental Research. 1992, vol. 16. No. 4, pp. 721-725.
Swift, R. M., "Transdermal measurement of alcohol consumption", Addiction, 1993, vol. 88, pp. 1037-1039.
Akin et al., "Alcohol Biosensing by Polyamidoamine (PAMAM)/ Cysteamine/Alcohol Oxidase-Modified Gold Electrode", 2009 American Institute of Chemical Engineers, vol. 26, No. 3, pp. 896-906.
Buono, Michael J., "Sweat Ethanol Concentrations Are Highly Correlated with Co-Existing Blood Values in Humans", Experimental Physiology (1999), vol. 84, pp. 401-404.
Gamellaa et al., "A novel non-invasive electrochemical biosensing device for in situ determination of the alcohol content in blood by monitoring ethanol in sweat", Analytica Chimica Acta, vol. 806, 2014, pp. 1-7.
Nyman et al., "The Elimination of Ethyl Alcohol in Sweat", Acta Physiologica, vol. 74, Issue 2, May 1936, pp. 155-159.
Anderson, Joseph C., "The kinetics of transdermal ethanol exchange", Journal American Physiological Society, vol. 100: pp. 649-655, 2006.
Hawthorne, U.S., "Transdermal Alcohol Measurement: A Review of The Literature", Canadian Society of Forensic Science Journal, vol. 39. No. 2, 2006, pp. 65-71.
Examination Report under Section 18 (3), United Kingdom Application No. GB 1522662.4, dated Jun. 29, 2016, 4 pages.
Examination Report under Section 18 (3), United Kingdom Application No. GB 1522662.4, dated Dec. 15, 2016, 3 pages.

\* cited by examiner

SKIN PATCH

CROSS-REFERENCE TO RELATED APPLICATIONS

This application is a U.S. national stage continuation application under 35 U.S.C. § 371 of International Patent Application No. PCT/GB2016/053977 filed on Dec. 16, 2016, which claims the benefit of Great Britain Patent Application No. 1522662.4 filed on Dec. 22, 2015, the contents of each of which are incorporated herein by reference.

TECHNICAL FIELD

The disclosure relates to skin patch for detecting a chemical in a perspiration fluid. In particular, the disclosure relates to a skin patch for monitoring alcohol or drug consumption by a subject.

BACKGROUND

Monitoring of alcohol and drug consumption comes into the spheres of both law enforcement and medicine.

In the sphere of law enforcement, offenders may have, as part of their sentence, an abstinence regime put in place. In this case the objective is to prevent consumption of substances that are known to trigger undesirable behaviours.

In medicine, there are two areas where monitoring of chemical substance may be needed. Firstly, there is a growing body of patients on a multi-medication regime who have specific numbers of medicines to take at certain times throughout the day. This group has a high probability of taking the wrong combinations of pills at the wrong time, even when employing self-dispensing machines. A device capable of reporting ingestion of the correct medicines automatically would be a great benefit to this group and their physicians. There exist a number of semi-automatic solutions for delivering medication at the correct time; however, these do not ensure that the patient has taken the correct doses at the correct time. Secondly, certain groups of patients need to detect a single substance other than medication. Such patients may be on an abstinence regime, or may be monitoring metabolic signs of metabolic malfunction. For example, recovering alcoholics constitute a group of abstainers who may wish to self-monitor. Individuals suffering from diabetes may want to perform real-time monitoring of their metabolic state.

In offender management regimes there is a new trend toward abstinence orders. The current state of the art in real-time alcohol monitoring involves a user being prompted to blow into an image-secured breathalyzer. Alternatively, the user is provided with a body mounted fuel-cell device which detects evaporating alcohol from the skin. Such systems rely on self-testing and/or suffer from a delayed system response. As a result, they have a limited capacity to prevent an undesirable behaviour occurring before detection. Both these devices are intended for offender management applications and cannot realistically be seen as a solution for those who want to stay sober under other circumstances.

The current state of the art in non-invasive drug monitoring is provided by an adhesive patch containing an absorbent paper that on removal undergoes laboratory examination by gas-chromatography and mass-spectroscopy for traces of known drugs. Such patches do not provide real-time information as they are sampled on a weekly basis, and then suffer a delay of a week or more before the laboratory results are available. Such a patch is only suitable for ensuring abstinence and does not allow a quick response for either law enforcement or medical purposes.

It is an object of the disclosure to address one or more of the above mentioned problems.

SUMMARY

According to a first aspect of the disclosure there is provided a chemical monitoring system comprising a skin patch for detecting an analyte in perspiration, comprising a first layer permeable to perspiration; a second layer coupled to the first layer, the second layer being adapted to receive the perspiration; wherein a property of the second layer changes upon receiving the analyte; a detector coupled to the second layer, adapted to detect parameter data indicative of the property of the second layer; and a processor adapted to receive the parameter data and to return an output indicative of a presence of an analyte in a subject's body based on the parameter data.

For example, the parameter data may comprise electrical parameter data such as impedance data or conductance data.

Optionally, the chemical monitoring system may comprise a housing comprising communication means. For example, the communication means may be a transmitter or an antenna suitable for transmitting parameter data.

Optionally, the housing may be removably coupled to the skin patch.

Optionally, the processor may be located within the housing.

Optionally, the processor may be located in a device remote from the skin patch.

Optionally, the detector may be part of the skin patch.

Optionally, the detector may be located within the housing.

Optionally, the skin patch may comprise a radio frequency device and the housing may comprise a reader for reading the radio frequency device For example the radio frequency device may comprise a radio frequency chip, also referred to as a radio frequency tag.

According to a second aspect of the disclosure there is provided a skin patch for use with in a chemical monitoring system according to the first aspect of the disclosure, comprising a first layer permeable to perspiration; a second layer coupled to the first layer, the second layer being adapted to receive the perspiration; wherein a property of the second layer changes upon receiving an analyte; and wherein the property of the second layer comprises at least one of a chemical property and an electrical property.

The following options are common to both first and second aspects of the disclosure.

Optionally, the skin patch comprises a detector coupled to the second layer, adapted to detect parameter data indicative of the property of the second layer. For example, the parameter data may comprise electrical parameter data such as impedance data or conductance data.

Optionally, the skin patch comprises a transmitter coupled to the detector, adapted to transmit the detected parameter data to a processor.

Optionally, the transmitter may comprise a radio frequency tag.

Optionally, the skin patch comprises a flexible electronic circuit coupled to the second layer.

Optionally, the detector may be adapted to detect the parameter data in real-time.

Optionally, the second layer may be functionalised.

Optionally, the second layer includes at least one of a polymer matrix, a gel matrix, and a polymer layer.

Optionally, the matrix or layer comprises a plurality of probes adapted to interact with the analyte such that an electrical property of the matrix or layer changes upon probe-analyte interaction. For example, the probe-analyte interaction may include at least one of a chemical reaction and a binding event.

Optionally, the plurality of probes comprises at least one of an oxidizing agent, an enzyme and a nanostructure.

Optionally, the first layer may be adapted to provide adhesion to a skin region of a subject.

Optionally, the detector includes an electrical detector.

Optionally, the electrical detector may be adapted to detect at least one of a capacitance, an inductance, a resistance, and a conductivity value of the second layer.

Optionally, the electrical detector comprises at least one electrode in contact with the second layer. For example, the electrical detector may be an impedance detector.

Optionally, the skin patch comprises an identifier.

Optionally, the skin patch comprises a tamper detection arrangement adapted to indicate interference with the patch. The tamper detection arrangement may comprise a perforation of at least one of the first layer and the second layer. The tamper detection arrangement may comprise generation of an electrical signal.

Optionally, the analyte includes ethanol.

According to a third aspect of the disclosure, there is provided a method of detecting an analyte in perspiration, comprising applying a skin patch comprising a second layer according to the second aspect of the disclosure, to a skin portion of a subject; detecting parameter data indicative of a property of the second layer; transmitting the parameter data to a processor; analysing the parameter data using the processor; outputting a result indicative of a presence of an analyte in the subject's body.

DETAILED DESCRIPTION

The disclosure is described in further detail below by way of example and with reference to the accompanying drawings, in which.

Figure 1:
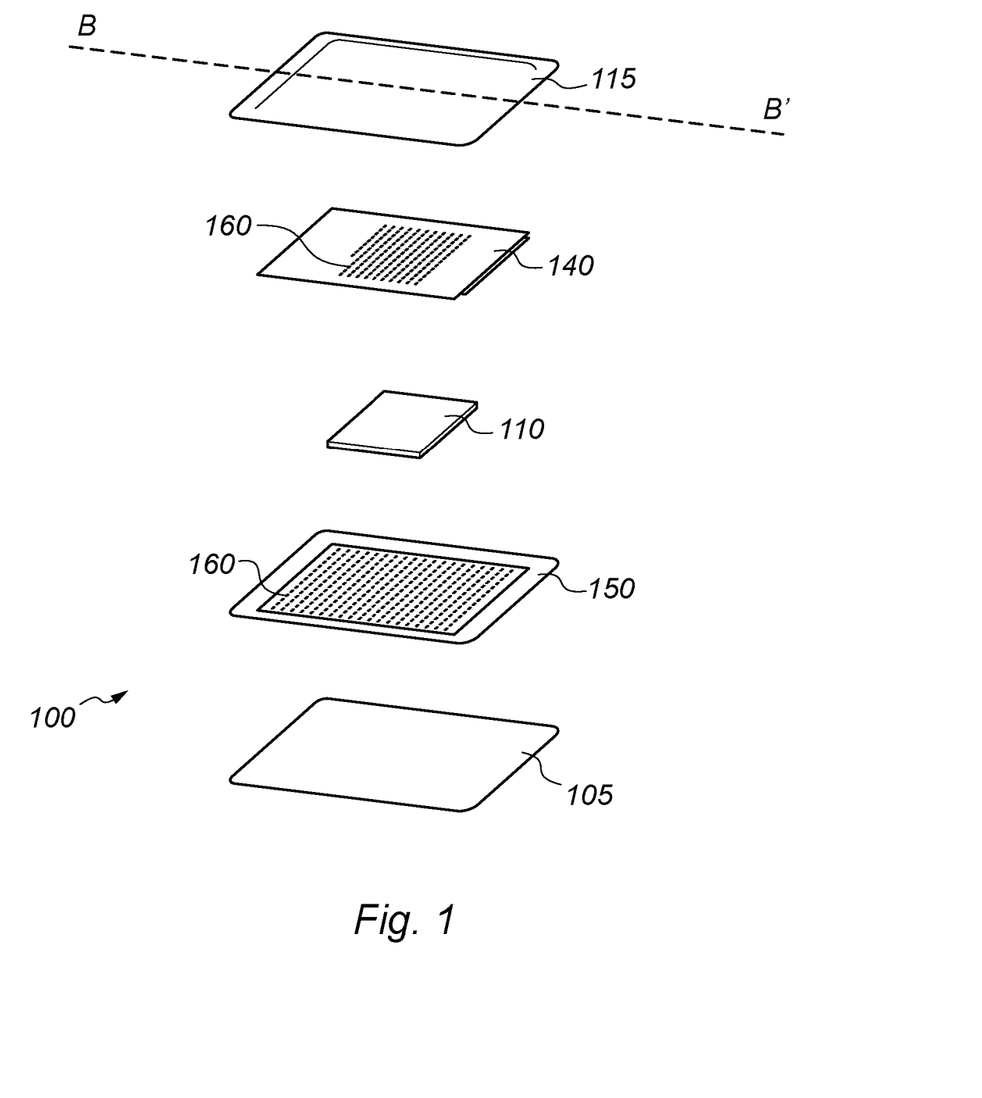
FIG. 1 is an exploded view of a skin patch for detecting a chemical.

FIG. 1 illustrates a skin patch 100 for detecting presence of a chemical in a perspiration fluid produced by the skin of a subject. In the context of the present description, perspiration may include chemical substance produced by sweat glands as well as chemical substance produced by sebaceous glands also referred to as sebum. The skin patch has a first layer 105, referred to as inner layer for contacting with a skin portion of the subject, a second layer 110, referred to as active layer for interacting with a chemical to be detected, and a third layer 115, referred to as outer layer. The active layer 110 is sandwiched between the inner layer 105 and the outer layer 115. In addition, the skin patch contains a flexible electronic circuit 140 located between the active layer 110 and the outer layer 115. Optionally the skin patch may be provided with an additional layer 150 located between the active layer 110 and the inner layer 105. The additional layer may be a reflective layer. The additional layer 150 and the flexible electronic circuit 140 are provided with a plurality of perforations 160 making them porous.

The inner layer 105 has a lower surface and an upper surface. The inner layer is attachable to the skin of a subject. In an exemplary embodiment the inner layer has an adhesive film (not shown) located on the lower surface of the inner layer, or of itself adheres to the skin. The inner layer is permeable to perspiration fluid. For example, the inner layer may be a polymer layer permeable to water and alcohol/ketones compounds present in perspiration.

Figure 2:
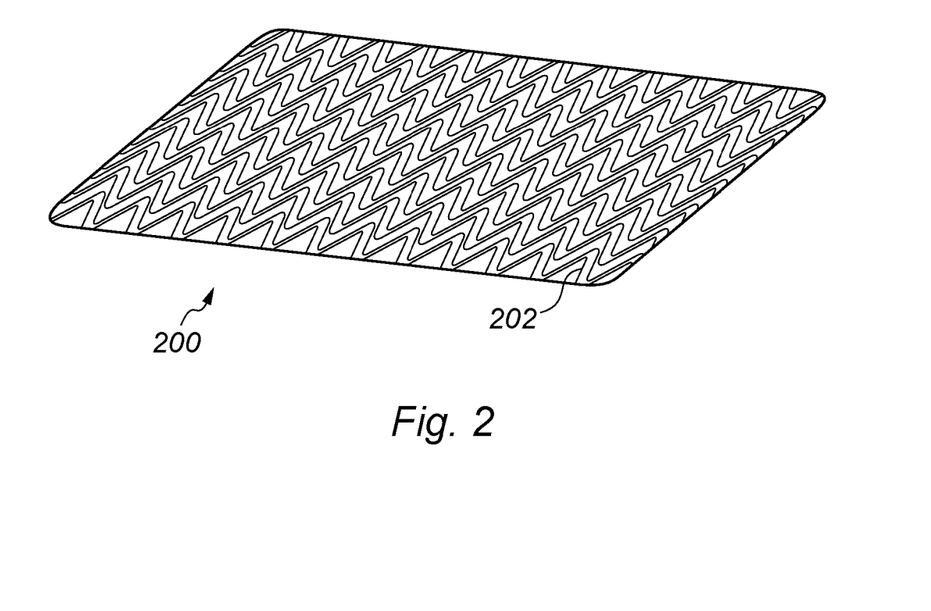
FIG. 2 is a perspective view of an inner layer comprising a tamper detection feature.

FIG. 2 shows a perspective view of an inner layer 200 comprising a tamper detection feature. In this case, the inner layer has a plurality of weakening lines 202. These features allow the inner layer to partially tear and/or delaminate on removal from the skin. Alternatively, an adhesive film of the inner layer may be patterned to provide different pulling forces across the inner layer, such that the inner layer is structurally deformed upon its removal from the skin.

Returning to FIG. 1, the active layer 110 comprises a medium capable of receiving a perspiration fluid containing water, and a chemical compound to be detected, referred to as analyte or target molecule. In a specific example the target compound is an alcohol or a ketone compound. The medium may be a molecular layer or a matrix such as a polymer matrix, a gel or a hydrogel or a conductive polymer. The medium may be functionalised with a specific probe or probes capable of binding to and/or to react with the target compound. For example, the probe may be an oxidizing agent for reacting with the analyte. In an exemplary embodiment, the probe may be a catalyst for catalysing a chemical reaction, such as a reaction of oxido-reduction, with the analyte. Such catalyst may be an enzyme such as an oxidoreductase. In another example, the probe may be a label molecule or a particle for example a nanoparticle quantum dot.

The active layer can be implemented as a gel/polymer matrix or a surface layer arranged to change impedance and/or conductivity upon interaction with the analyte/target compound.

In a first example, the active layer is made at least in part of a film or matrix containing an oxidizing agent such as potassium dichromate $K_2Cr_2O_7$. In this case, ethanol C2H5OH, is oxidised by potassium dichromate to acetic acid $CH_3COOH$, according to the following reaction:

$$2K_2Cr_2O_7 + 3C_2H_5OH + 8H_2SO_4 \xrightarrow{\text{AgNO}_3 \text{ catalyst}} 2CR_2(SO_4)_3 + 3CH_3COOH + 2K_2SO_4 + 11H_2O$$

As the oxidising agent potassium dichromate is reduced to chromium sulfate $Cr_2(SO_4)_3$, the active layer undergoes an electrical change. The acetic acid is used to change the gel matrix chemical nature. For instance, acetic acid can be used to replace a soluble salt with an insoluble acetate.

In a second example, the active layer is made at least in part of a film or matrix containing an enzyme belonging to the family of oxidoreductases, such as alcohol oxidase. Alcohol oxidase, AOX may be immobilised on the film or matrix, for example a conducting polymer film such as a polyaniline film. Alternatively, alcohol oxidase may be immobilised within a gel matrix such as a hydrogel. Alcohol oxidase oxidizes ethanol to acetaldehyde and hydrogen peroxide according to the following reaction:

In this case, hydrogen peroxide can interact with an organic compound present in the layer or matrix hence creating a change in capacitance or conductance in the active layer. The organic compound may have a plurality of oxidation states, in which each oxidation state experience a different electrical conductivity. For example, the organic compound may be polyaniline. Optionally, the gel/polymer matrix may contain an agent designed to chemically remove substances that may interfere with the detection of the analyte. For example, substances like acetone, methanol or bleach, may interfere with the detection of ethanol. Alternatively, this chemical removal mechanism may be housed in a layer located between the skin and the gel/polymer layer. The chemical removal mechanism may also be combined with or embedded into the inner layer.

In a third example, the active layer is made at least in part of a film or matrix containing a nanostructure. The nanostructure may be a two-dimensional structure such as a quantum well, a one-dimensional structure such as a quantum wire, or a zero-dimensional structure such as a quantum dot. The nanostructure or plurality of nanostructures may be functionalised to conduct electrons upon binding to a target compound. For example, the nanostructure may be functionalised with a layer of molecules that changes an energy level of the conduction band of the nanostructure. The energy level of the conduction band may be lowered upon binding of the target onto the layer of molecules such that an electron in the valence band can be promoted to the conduction band either instantly or upon applying a voltage across the active layer.

In an embodiment the active layer 110 may be designed to generate a predicable electrical change upon addition of the analyte. In other words, the active layer 110 follows a known response curve. Using this approach, it is possible to monitor analyte levels over an extended period of time. In this case a level of analyte present in a subject may be obtained by monitoring an electrical change, for example a change in impedance, of the active layer 110 within a period of time. In an alternative embodiment the active layer is designed to be replaced after a single interaction with the analyte. In yet another embodiment, the active layer is coupled to a microfluidic device for delivering a cleaning agent to the active layer. In this case the active layer may be cleaned by removing the target compounds present in the active layer using the cleaning agent.

The outer layer 115 comprises a membrane, or a plurality of membranes, allowing water to be transported out of the patch whilst limiting its ingress during an eventual submersion. Additionally, the outer layer 115 may comprise a machine readable pattern containing a unique identifier. An additional layer (not shown) may be located between the active layer 110 and the inner layer 105 of the patch to prevent components of the active layer leaching though the inner layer into the skin.

The flexible circuit 140 has a plurality of internal components or modules for performing different functions. In an exemplary embodiment, the flexible circuit has a receiver/transmitter for communication with an electronic device and a readout circuit for reading detector data such as data from an electronic detector such as an impedance detector. The readout circuit may be implemented to transform the detector data into a format suitable for transition to an external device. The flexible circuit may also be equipped with an identification circuit for delivering either an RF signature or a digital signature. The readout circuit and or the identification circuit may include a Radio-Frequency identification, RFID chip. The flexible circuit may also be provided with a control circuit for controlling the detector.

The flexible circuit 140 may be printed onto a substrate of insulating material. The substrate material includes perforations 160 over a single area or a plurality of areas which do not contain electrical connections. Such perforations 160 may take the form of cut-outs, multiple holes of millimetre scale (of the order of 0.1 to 1 of millimetres), or microscopic pores. In an exemplary embodiment, connections present within the circuit between different electronic components of the circuit may be protected from interference from electrolytes present in sweat by the addition of at least one additional polymer layer. The flexible circuit 140 may be mounted with an electrical power source. The power source may be a battery. Alternatively, electrical power may be based on an energy harvesting system; for example, a system capable of converting energy available in the surrounding environment of the patch. In a specific example the energy harvesting system is an electromagnetic wave harvesting system such as an RF harvesting system. The circuit does not require external connections. For this reason, it can be sealed off to prevent ingress of water and salts.

Figure 3:
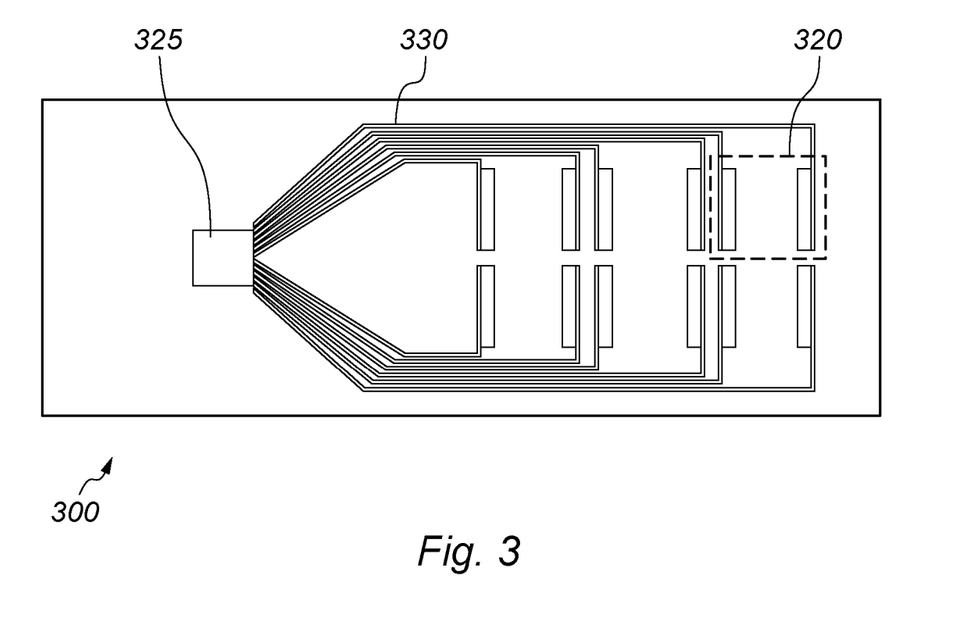
FIG. 3 is a top view of a flexible electronic circuit.

FIG. 3 shows a top view of a flexible electronic circuit 300 suitable for measuring the presence of an analyte electrically. The electronic circuit has detection circuit formed by six pairs of electrodes 320, for interrogating a corresponding area of the active layer. Each electrode is connected to a control chip 325 by a conductive path 330. At least one of the electrode present on the circuit may be used as a reference electrode. Alternatively, or in combination, a silvered layer may be mounted on the inner layer to provide an earth plane/ground for the electrodes present on the flexible circuit. As mentioned above, the flexible electronic circuit may contain other electronic components (not shown) in addition to the detection circuit, such as a power circuit, a temperature sensor and a detection module for communicating with an external device.

When mounted inside the skin patch, the electrodes of the flexible circuit are in contact with a region of the detection-medium of the active layer. If the active layer is designed to detect a single analyte, then the signal detected by the electrodes can be averaged. In case the active layer is designed to detect multiple analytes, the detection medium has multiple regions corresponding to the detection of specific analytes. In this case the design of the active layer matches the design of the electrodes such that a location of an electrode or electrodes is in contact with a specific region of the active layer corresponding to region for measuring a particular analyte.

Additionally, the active layer may be shielded from external light in order to reduce noise generated by optical excitation. In an alternative embodiment the detection circuit may be mounted on two layers on either side of the detection medium.

The electrodes of the detection circuit may be designed to measure an impedance of the active layer. In this case both the capacitive and resistive components of the impedance may be used for detecting an electrical and/or chemical change in the active layer. This approach may be used to reduce noise signal induced by salt and other electrolytes contained in sweat.

The outer layer 115 may be provided with conductive pads in electrical communication with the electrodes 320. In this case, a current and/or voltage may be provided to the electrodes 320 via the conductive pads. In this case the outer layer 115 may be treated to alter its own electrical impedance characteristics. Alternatively, or in combination, the outer layer 115 may be provided with an aperture allowing to access a region of the flexible circuit.

Figure 4:
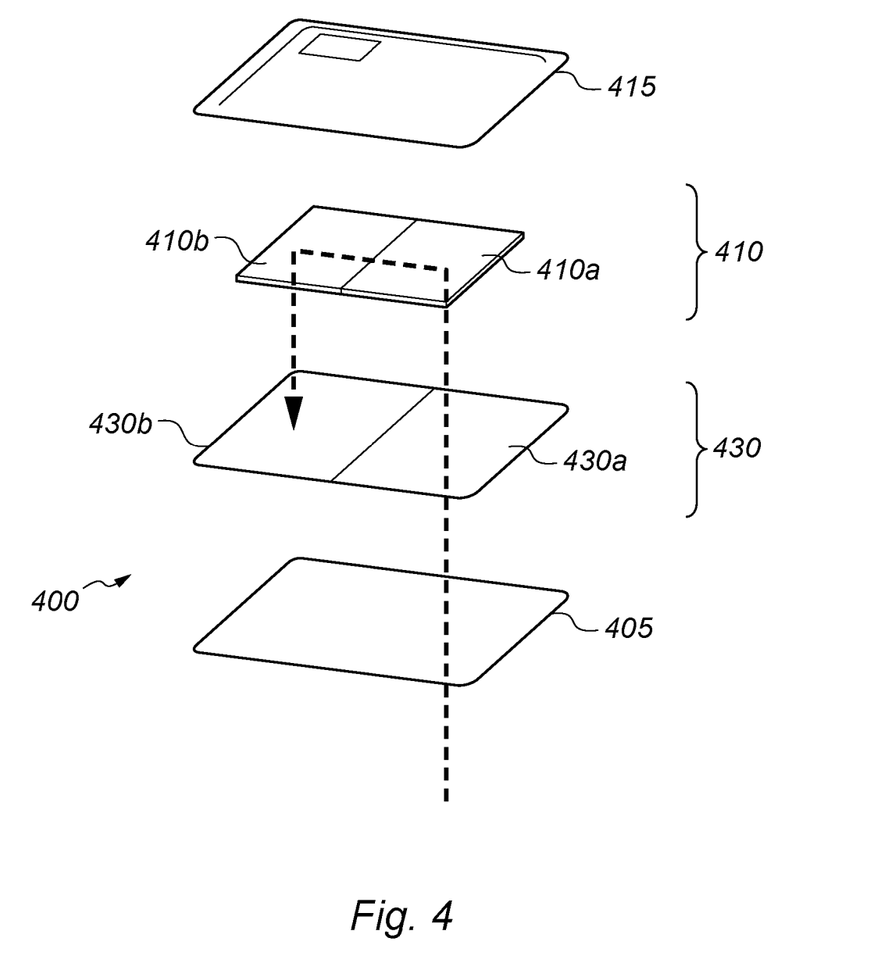
FIG. 4 is an exploded view of a skin patch according to an exemplary embodiment.

FIG. 4 shows a simplified view of a skin patch having an inner layer 405, an outer layer 415, an active layer 410 and a fourth layer 430. For clarity, the flexible electronic circuit has been omitted. The active layer 410 has two parts: a detection part 410a and a hygroscopic part 410b. The role of the hygroscopic part 410b is to attract the sweat through the detection part 410a. For example, the hygroscopic part 410b may be made, at least in part, of silica gel or Bentonite clay. The fourth layer 430, is located between the inner layer 405 and the active layer 410. The fourth layer has a porous part 430a adjacent to an impervious part 430b also referred as non-porous part. The detection part 410a of the active layer 410 is above the porous part 130a of the fourth layer. The surface area of the detection part 410a is smaller or equal to the surface area of the porous part 430a, such that the detection part 410a overlaps entirely with an area of the porous part 430a. The hygroscopic part 410b of the active layer is above the impervious part 430b of the fourth layer 430. The surface area of the hygroscopic part 410b is smaller or equal to the surface area of the non-porous part 430b, such that the hygroscopic part 410b overlaps entirely with an area of the non-porous part 430b. The dotted arrow in FIG. 4 represents a direction of propagation of a perspiration fluid through the skin patch. Sweat is drawn from the skin of the subject towards the hygroscopic part 410b through the inner layer 405, the porous part 430a and the detection part 410a. The impervious part 430b then prevents the sweat from returning to the inner layer 405. In FIG. 4, the hygroscopic part 410b is located adjacent to the detection part 410a. However, in an alternative embodiment the hygroscopic part 410b may be located above the detection part 410a.

Figure 5:
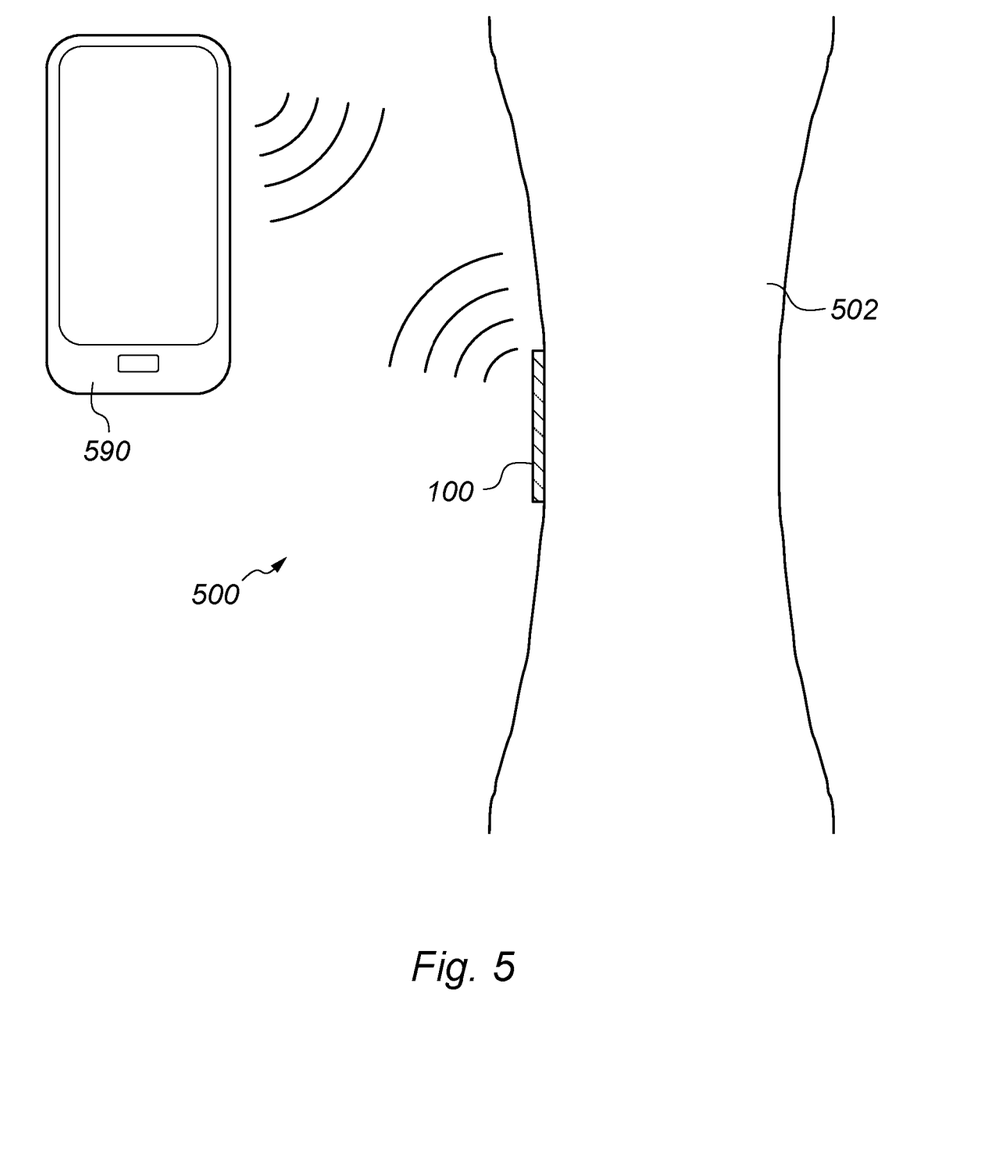
FIG. 5 is a schematic representation of a chemical monitoring system.

FIG. 5 shows a schematic representation of a chemical monitoring system. A skin patch 100 is attached to a subject's ankle 502. The skin patch is internally powered and communicates with an electronic device 590. The electronic device 590 can be for instance: a device intended for personal monitoring, including GSM enabled personal alarm systems, a computational device or a mobile telephonic device.

Figure 6:
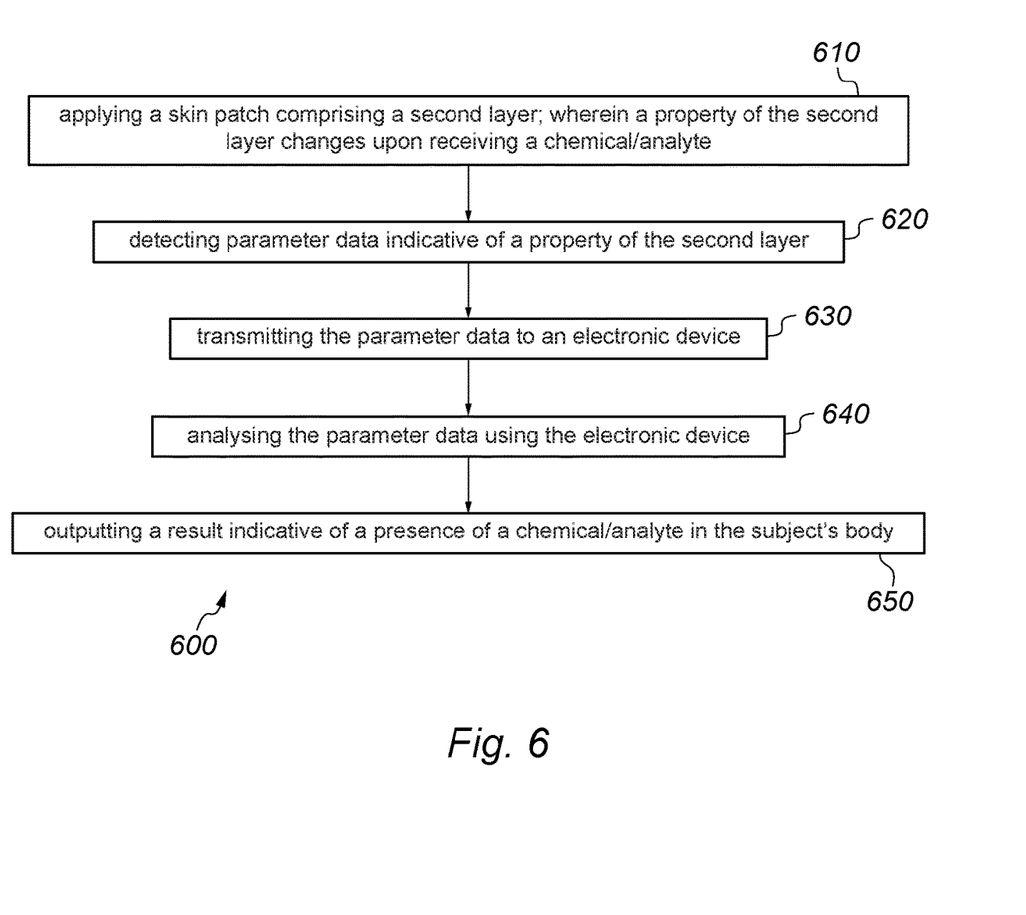
FIG. 6 is a flow diagram of a method for monitoring presence of a chemical using the chemical monitoring system of FIG. 5.

FIG. 6 shows a flow diagram of a method 600 for monitoring presence of a chemical/analyte using a skin patch as described with reference to FIGS. 1 to 5. At step 610, the skin patch 100 is applied to a skin portion of a subject. Perspiration passes through the porous inner layer 105 into the active layer 110. Upon interaction with a specific analyte, for example ethanol, contained in the perspiration fluid of the patient, the layer or gel matrix of the active layer 110 experiences a change in its chemical and/or electrical property. At step 620, the detector detects a parameter of the active layer. In practice an electronic device 590 sends a signal to the skin patch 100 to start measuring a physical property of the active layer 110. On receipt of this signal, the electronic circuit 140 performs a routine procedure. Considering an electrical detector comprising a plurality of electrodes 320, a voltage and or a current is applied to the electrodes 320 to perform an electrical measurement. For example, the electrical measurement may be an impedance measurement. In this case a plurality of measurement may be performed at different oscillation frequencies. Alternatively, the electrical measurement may be a conductivity measurement. At step 630, the parameter data collected by the electrical detector, such as impedance data or conductance data, are then codified and transmitted to the electronic device 590. At step 640, the electronic device 590 performs an analysis of the parameter data and returns at step 650 a result indicative of the presence or absence of the analyte in the subject's sweat. The steps 620 to 650 may be repeated at regular time intervals. In this case the external device 590 may perform analysis of differences in measured analyte response from measurement to measurement. Alternatively, or in combination, the external device may transmit the measurement signal to a remote data handling system.

Using such a method allows determining the presence or absence of a specific target molecule in the subject's sweat in real-time. In other words, information regarding ingestion of the target compounds by the subject can be observed substantially as it happens.

Figure 7:
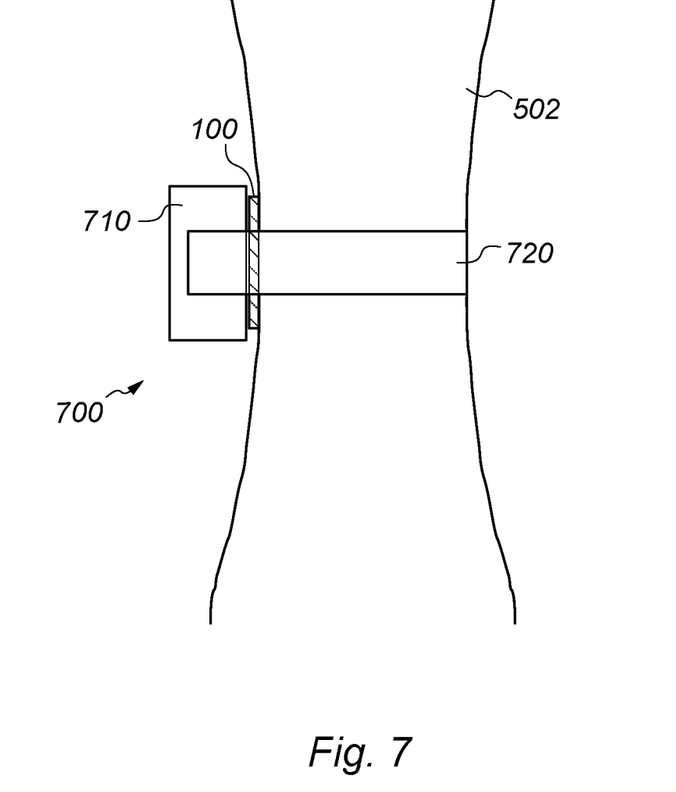
FIG. 7 is schematic representation of another chemical monitoring system.

FIG. 7 shows another schematic representation of a chemical monitoring system 700. In this case, the skin patch 100 is removably coupled to an electronic device 710 secured to a subject's ankle 502 by a strap 720.

The electronic device 710 has a housing which may contain a power supply for powering the flexible circuit 140 of the skin patch 100 and an electronic circuit for collecting electronic data generated by the detector of the skin patch 100. In some embodiment, the housing of the electronic device 710 may have a memory and a processor for analysing the data. The housing of the electronic device 710 can also include a communication means such as a communication module for transmitting an analyte result to the subject and/or to another device.

In an exemplary embodiment, the skin patch 100 and the electronic device 710 are coupled using a close coupled resonant loop system allowing power and signals to be transferred from the electronic device to the skin patch and signals to be transferred from patch to the electronic device 710. For example, the close coupled resonant loop system may be an RFID coupling mechanism having an RFID tag mounted on the patch and a reader provided on the electronic device. The type of coupling may be based on backscatter coupling. In a specific example the RFID tag is configured to change its impedance depending on a change in a chemical or an electronic property of the second layer upon interaction of the second layer with the analyte. For example, the RFID tag may have an integrated circuit, an antenna, and at least one electrode for measuring an electrical parameter of the second layer.

Coupling of the electronic device with the skin patch may require a degree of alignment. To facilitate alignment, the electronic device and/or the patch can be provided with a reference feature, for example a reference line or a mechanical arrangement. The skin patch and the electronic device may also be provided with an electronic connector. In this case a location of the electronic device with respect to the patch would be confirmed once the electrical connection has been achieved.

The electronic device 710 may take the form of a paired device intended for personal monitoring, including GSM enabled personal alarm systems. The paired device may take the form of an electronic device adapted to receive data from the patch when the user comes into proximity with the electronic device. For example, data may be transferred from the patch to the paired device when the patch is within a few centimetres from the paired device. Where the paired device is an offender management tag, the patch may be placed on the outside of the leg just above the ankle with the tag electronics box covering the patch; the underside of the electronics box containing a matched coil/antenna circuit to transfer power to the patch and obtain returning signals.

A skilled person will appreciate that variations of the disclosed arrangements are possible without departing from the disclosure. Accordingly, the above description of the specific embodiment is made by way of example only and not for the purposes of limitation. It will be clear to the skilled person that minor modifications may be made without significant changes to the operation described.

The invention claimed is:

1. A chemical monitoring system comprising:
   a skin patch for detecting ethanol in perspiration, the skin patch comprising a first layer permeable to perspiration fluid, the first layer being adapted to provide adhesion to a skin region; an electrical detector; a second layer located between the first layer and the electrical detector, wherein the second layer is adapted to receive the perspiration fluid via the first layer, and wherein a property of the second layer changes upon receiving ethanol; the second layer being made at least in part of a film or matrix comprising alcohol oxidase; the electrical detector being adapted to detect parameter data indicative of the property of the second layer; a third layer located between the first layer and the second layer, the third layer having a surface comprising a porous part adjacent to an impervious part to direct a flow of the perspiration fluid towards the second layer;
   wherein the electrical detector is further adapted to detect the change in the property of the second layer by detecting at least one of a capacitance, an inductance, a resistance, and a conductivity value of the second layer; and
   the chemical monitoring system further comprising a processor adapted to receive the parameter data and to return an output indicative of a presence of ethanol in a subject's body based on the parameter data.

2. The chemical monitoring system as claimed in claim 1, further comprising a housing comprising communication means; wherein the housing is removably coupled to the skin patch.

3. The chemical monitoring system as claimed in claim 2, wherein the processor is located within the housing or wherein the processor is located in a device remote from the skin patch.

4. The chemical monitoring system as claimed in claim 2, wherein the skin patch comprises a radio frequency device and wherein the housing comprises a reader for reading the radio frequency device.

5. A skin patch for detecting ethanol in perspiration, comprising:
   a first layer permeable to perspiration fluid, the first layer being adapted to provide adhesion to a skin region;
   an electrical detector;
   a second layer located between the first layer and the electrical detector, wherein the second layer is adapted to receive the perspiration fluid via the first layer, wherein a property of the second layer changes upon receiving ethanol; the second layer being made at least in part of a film or matrix comprising alcohol oxidase;
   a third layer located between the first layer and the second layer, the third layer having a surface comprising a porous part adjacent to an impervious part to direct a flow of the perspiration fluid towards the second layer;
   wherein the electrical detector is adapted to detect parameter data indicative of the property of the second layer, and wherein the electrical detector is further adapted to detect the change in the property of the second layer by detecting at least one of a capacitance, an inductance, a resistance, and a conductivity value of the second layer.

6. The skin patch as claimed in claim 5, further comprising a transmitter coupled to the electrical detector, adapted to transmit the detected parameter data to a processor; optionally wherein the transmitter comprises a radio frequency tag.

7. The skin patch as claimed in claim 5, further comprising a flexible electronic circuit coupled to the second layer.

8. The skin patch as claimed in claim 5, wherein the detector is adapted to detect the parameter data in real-time.

9. The skin patch as claimed in claim 5, wherein the second layer is functionalised.

10. The skin patch as claimed in claim 5, wherein the second layer includes at least one of a polymer matrix, a gel matrix, and a polymer layer.

11. The skin patch as claimed in claim 10, wherein the matrix or layer comprises a plurality of probes adapted to interact with ethanol such that an electrical property of the matrix or layer changes upon probe-analyte interaction; wherein the probe-analyte interaction includes at least one of a chemical reaction on and a binding event.

12. The skin patch as claimed in claim 11, wherein the plurality of probes comprises at least one of an oxidizing agent, an enzyme and a nanostructure.

13. The skin patch as claimed in claim 5, wherein the property of the second layer comprises at least one of a chemical property and an electrical property.

14. The skin patch as claimed in claim 5, wherein the electrical detector comprises at least one electrode in contact with the second layer, and/or wherein the electrical detector is an impedance detector adapted to detect the change in the property of the second layer by detecting an impedance value of the second layer.

15. The skin patch as claimed in claim 5, further comprising an identifier.

16. The skin patch as claimed in claim 5, further comprising a tamper detection arrangement adapted to indicate interference with the patch.

17. The skin patch as claimed in claim 16, wherein the tamper detection arrangement comprises a perforation of at least one of the first layer and the second layer, and/or wherein the tamper detection arrangement comprises generation of an electrical signal.

18. The skin patch as claimed in claim 5, wherein the second layer comprises a hygroscopic portion.

19. A method of detecting ethanol in perspiration, comprising:
   applying a skin patch for detecting ethanol in the perspiration to a skin of a subject, wherein the skin patch comprises a first layer permeable to perspiration fluid, the first layer being adapted to provide adhesion to the skin region; an electrical detector; a second layer located between the first layer and the electrical detector, wherein the second layer is adapted to receive the perspiration fluid via the first layer; wherein a property of the second layer changes upon receiving ethanol; the second layer being made at least in part of a film or matrix comprising alcohol oxidase; and a third layer located between the first layer and the second layer, the third layer having a surface comprising a porous part adjacent to an impervious part to direct a flow of the perspiration fluid towards the second layer;
and wherein the electrical detector is adapted to detect parameter data indicative of the property of the second layer;
detecting parameter data indicative of a property of the second layer by detecting at least one of a capacitance, an inductance, a resistance, and a conductivity value of the second layer;
transmitting the parameter data to a processor;
analysing the parameter data using the processor; and
outputting a result indicative of a presence of ethanol in the subject's body.

\* \* \* \* \*